United States Patent
Stein et al.

(10) Patent No.: US 8,690,929 B2
(45) Date of Patent: Apr. 8, 2014

(54) ORTHOPEDIC SCREW FOR MEASURING A PARAMETER OF THE MUSCULARSKELETAL SYSTEM

(75) Inventors: Marc Stein, Chandler, AZ (US); Martin Roche, Fort Lauderdale, FL (US)

(73) Assignee: Orthosensor Inc., Dania Beach, FL (US)

( * ) Notice: Subject to any disclaimer, the term of this patent is extended or adjusted under 35 U.S.C. 154(b) by 471 days.

(21) Appl. No.: 12/826,273

(22) Filed: Jun. 29, 2010

(65) Prior Publication Data

US 2010/0331894 A1 Dec. 30, 2010

Related U.S. Application Data

(60) Provisional application No. 61/221,761, filed on Jun. 30, 2009, provisional application No. 61/221,767, filed on Jun. 30, 2009, provisional application No. 61/221,779, filed on Jun. 30, 2009, provisional application No. 61/221,788, filed on Jun. 30, 2009, provisional application No. 61/221,793, filed on Jun. 30, 2009, provisional application No. 61/221,801, filed on Jun. 30, 2009, provisional application No. 61/221,808, filed on Jun. 30, 2009, provisional application No. 61/221,817, filed on Jun. 30, 2009, provisional application No. 61/221,867, filed on Jun. 30, 2009, provisional application No. 61/221,874, filed on Jun. 30, 2009, provisional application No. 61/221,879, filed on Jun. 30, 2009, provisional application No. 61/221,881, filed on Jun. 30, 2009, provisional application No. 61/221,886, filed on Jun. 30, 2009, provisional application No. 61/221,889, filed on Jun. 30, 2009, provisional application No. 61/221,894, filed on Jun. 30, 2009, provisional application No. 61/211,901, filed on Jun. 30, 2009, provisional application No. 61/221,909, filed on Jun. 30, 2009, provisional application No. 61/221,916, filed on Jun. 30, 2009, provisional application No. 61/221,923, filed on Jun. 30, 2009, provisional application No. 61/221,929, filed on Jun. 30, 2009.

(51) Int. Cl.
  *A61B 17/86* (2006.01)
  *A61N 1/00* (2006.01)
  *A61B 5/05* (2006.01)

(52) U.S. Cl.
  USPC .......................... 606/301; 607/116; 600/410

(58) Field of Classification Search
  USPC .................. 411/411–416; 600/410–411, 448; 606/60, 246–279, 300–331; 607/115–116
  See application file for complete search history.

(56) References Cited

U.S. PATENT DOCUMENTS 4,127,110 A * 11/1978 Bullara ........................ 600/561
5,197,488 A    3/1993 Kovacevic (Continued)

*Primary Examiner* — Christopher Beccia

(57) ABSTRACT

A dual-mode closed-loop measurement system (100) for capturing a transit time, phase, or frequency of energy waves propagating through a medium (122) is disclosed. A first module comprises an inductor drive circuit (102), an inductor (104), a transducer (106), and a filter (110). A second module housed in a screw (335) comprises an inductor (114) and a transducer (116). The screw (335) is bio-compatible and allows an accurate delivery of the circuit into the muscularskeletal system. The inductor can be attached and interconnected on a flexible substrate (331) that fits into a cavity in the screw (335). The first and second modules are operatively coupled together. The first module provides energy to power the second module. The second module emits an energy wave into the medium that propagates to the first module. The transit time of energy waves is measured and correlated to the parameter by known relationship.

16 Claims, 8 Drawing Sheets

(56) References Cited

U.S. PATENT DOCUMENTS

| | | |
|---|---|---|
| 5,470,354 A | 11/1995 | Hershberger et al. |
| 5,683,396 A | 11/1997 | Tokish et al. |
| 5,688,279 A | 11/1997 | McNulty et al. |
| 5,871,018 A | 2/1999 | Delp et al. |
| 6,171,252 B1 | 1/2001 | Roberts |
| 6,245,109 B1 | 6/2001 | Mendes et al. |
| 6,583,630 B2 | 6/2003 | Mendes et al. |
| 6,621,278 B2 | 9/2003 | Ariav |
| 6,701,174 B1 | 3/2004 | Krause et al. |
| 6,714,763 B2 | 3/2004 | Hamel et al. |
| 6,821,299 B2 | 11/2004 | Kirking et al. |
| 6,856,141 B2 | 2/2005 | Ariav |
| 7,001,346 B2 | 2/2006 | White |
| 7,097,662 B2 | 8/2006 | Evans et al. |
| 7,195,645 B2 | 3/2007 | Disilvestro et al. |
| 7,256,695 B2 | 8/2007 | Hamel et al. |
| 7,295,724 B2 | 11/2007 | Wang et al. |
| 7,442,196 B2 | 10/2008 | Fisher et al. |
| 7,575,602 B2 | 8/2009 | Amirouche et al. |
| 7,578,821 B2 | 8/2009 | Fisher et al. |
| 7,587,945 B2 | 9/2009 | Crottet et al. |
| 7,615,055 B2 | 11/2009 | DiSilvestro |
| 7,632,283 B2 | 12/2009 | Heldreth |
| 2002/0029784 A1 | 3/2002 | Stark et al. |
| 2005/0020941 A1 | 1/2005 | Tarabichi |
| 2006/0058798 A1 | 3/2006 | Roman et al. |
| 2006/0232408 A1 | 10/2006 | Nyez et al. |
| 2006/0271112 A1 | 11/2006 | Martinson et al. |
| 2007/0219561 A1 | 9/2007 | Lavalle et al. |
| 2007/0233065 A1* | 10/2007 | Donofrio et al. ............... 606/61 |
| 2007/0272747 A1 | 11/2007 | Woods et al. |
| 2008/0228231 A1* | 9/2008 | Raphael et al. ............... 606/301 |

* cited by examiner

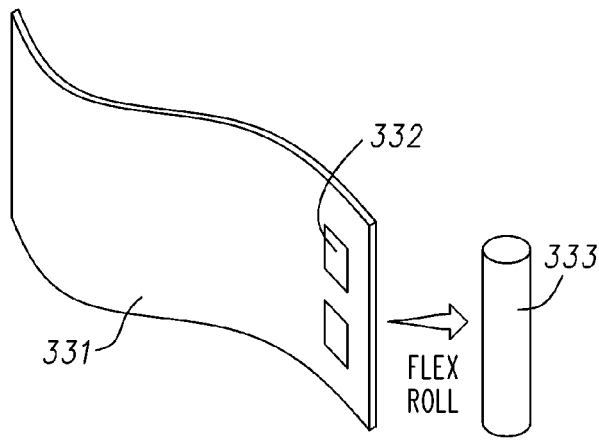
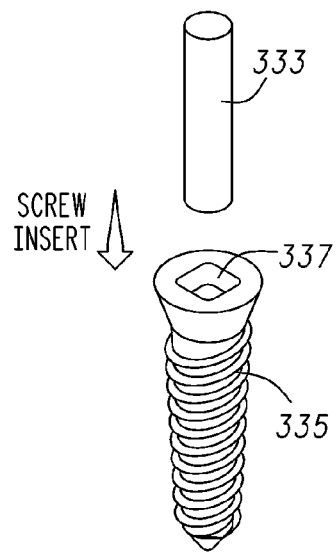
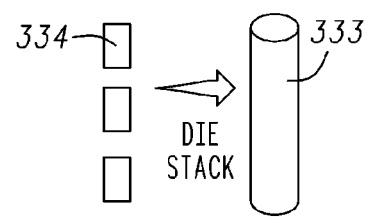
Fig. 3
Fig. 4
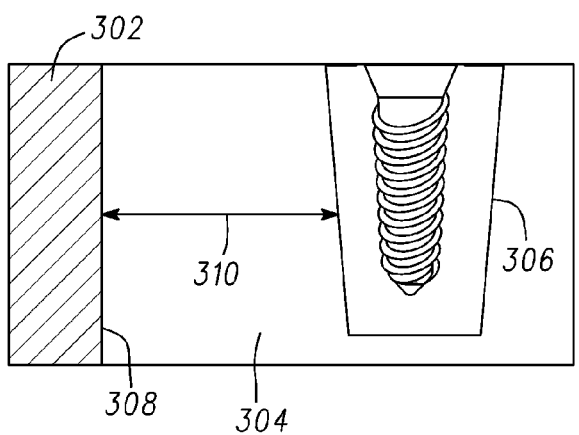
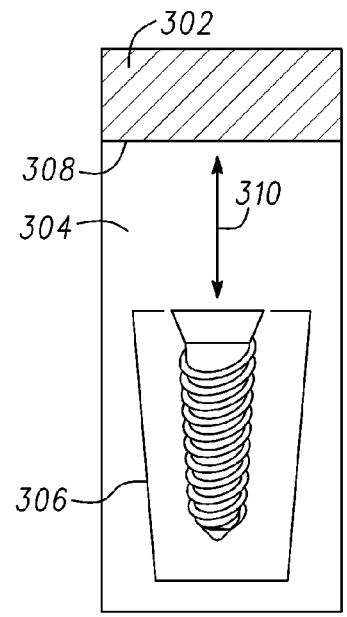
Fig. 5
Fig. 6

1100

ORTHOPEDIC SCREW FOR MEASURING A PARAMETER OF THE MUSCULARSKELETAL SYSTEM

CROSS-REFERENCE TO RELATED APPLICATIONS

This application claims the priority benefit of U.S. provisional patent application Nos. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009; the disclosures of which are hereby incorporated herein by reference in their entirety.

FIELD

The present invention relates generally to measurement of physical parameters, and more particularly, dual mode real-time measurement of physical parameters by evaluating changes in a transit time or propagating energy waves.

BACKGROUND

Sensors are used to measure or monitor a parameter. Sensors can provide quantitative information on the parameter or how the parameter changes over time. For example, a temperature sensor is commonly used to monitor the operating temperature of a component or a biological entity. The temperature sensor can be used to monitor temperatures over a variety of operating conditions and formats. Typically, sensor data is used in the assessment of an object or to monitor performance in different operational modes and environmental factors. Sensors can trigger an action such as turning off the system or modifying operation of the system in response to the measured parameter.

In general, cost typically increases with the measurement precision of the sensor. Cost can limit the use of highly accurate sensors in price sensitive applications. Furthermore, there is substantial need for sensors that have low power usage for systems that are battery operated. Ideally, the sensing technology used in a temporarily powered application will not significantly reduce the operating time of the device. Moreover, a high percentage of battery-operated devices are portable devices comprising a small volume and low weight. Device portability can place further size and weight constraints on the sensor technology used. Thus, form factor, power dissipation, cost, and measurement accuracy are important criteria that are evaluated when selecting a sensor or measurement system for a specific application.

BRIEF DESCRIPTION OF DRAWINGS

Various features of the system are set forth with particularity in the appended claims. The embodiments herein, can be understood by reference to the following description, taken in conjunction with the accompanying drawings, in which:

FIG. 3 is an exemplary illustration for screw sensor construction via flex rolling or die stacking in accordance with one embodiment;

FIG. 4 is an exemplary illustration of screw sensor construction via flex rolling or die stacking insertion in accordance with one embodiment;

FIG. 5 is an illustrative embodiment of the screw sensor as used in the dual mode closed loop measurement system in accordance with one embodiment;

FIG. 6 is an illustrative embodiment of the screw sensor as used in the dual mode closed loop measurement system in accordance with one embodiment;

DETAILED DESCRIPTION

Figure 1:
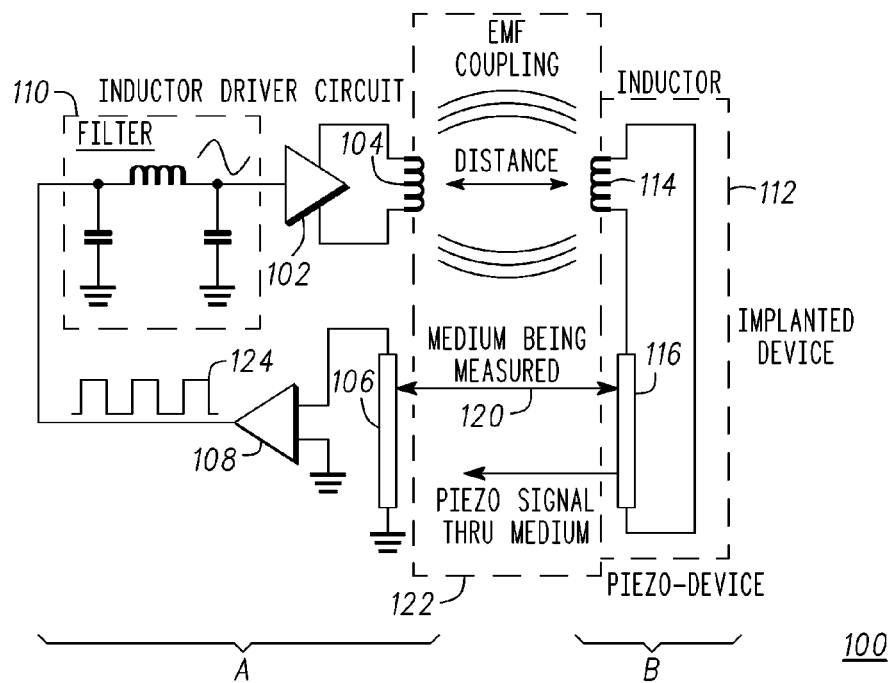
FIG. 1 is a schematic diagram of a dual mode closed loop measurement system in accordance with one embodiment.

Embodiments of the invention are broadly directed to wireless transmission coupling between a first device and a second device together forming a measurement system to measure one or more properties of a material between the first device and the second device.

The following description of exemplary embodiment(s) is merely illustrative in nature and is in no way intended to limit the invention, its application, or uses.

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

In one embodiment, a dual-mode closed loop measurement system evaluates a transit time of energy waves or pulses between two wireless modules. The measurement system can be integrated into medical devices to facilitate the measurement of physical or physiologic parameters within or affecting the interface between one or more of the medical devices and surrounding, but not limited to, tissue, bones, cartilage, fluids, or combinations thereof. Wireless modules may also be integrated into one or more of the medical devices to facilitate the measurement of physical or physiologic parameters of interest external to the medical devices having proximity, contacting, or sensing surfaces In this embodiment, one of the wireless modules functions as a master, actively providing power and control, and the other wireless module functions as a slave, passively receiving power and responding to the master. The first wireless module operating as the master can include a propagation tuned oscillator, digital logic, counters, and a phase detector for providing closed loop feedback. The first wireless module and second wireless module can operate over a same transmission type over both legs of the wireless transmission coupling, such as piezo-to-piezo, or over a mixed transmission type, for example, piezo-to-piezo and inductor-to-inductor. Operating inductor-to-inductor on one leg of the wireless transmission coupling path provides the benefit of improved energy efficiency. In the later case, dual mode closed loop operation is established by inductive coupling on a first leg of the wireless transmission coupling path and energy wave propagation on a second leg of the wireless transmission coupling path.

In this configuration, an inductor drive circuit on the first device actively initiates by way of a transmit inductor a query via inductive coupling to a receive inductor on the second device via the first leg (or path), the receive inductor in response to the query triggers a piezo component also on the second device to actively emit an energy wave that is propagated back to the first device through the propagation medium to be measured. The second device responsive to receiving the energy wave monitors the received energy wave for assessing the one or more properties of the propagation medium, whilst generating a pulse sequence that is fed back to the inductor drive circuit to create a close-loop feedback path. In this arrangement, the first device and the second device operate together via inductive coupling and energy wave propagation to form the dual-mode closed loop measurement system.

In another embodiment, the dual-mode closed loop measurement system constitutes in part a medical diagnostic system for assessing clinical implant parameters, for example, bone re-growth integrity, cartilage, fluids, tissue, bond strength, glue joint integrity, and general biological integrity with respect to one or more implanted prosthetic components, for example, orthopedic knee joint, hip or shoulder implants. In general, the first and second devices are each placed in a housing that can be placed in proximity, attached to, or inserted in the muscular-skeletal system. In this embodiment, the first device can be inserted in a bone screw, for example, by flex rolling of the electrical components on a flexible interconnect and insertion in a hollow portion of the screw, or by die stacking of the electrical components in the hollow portion of the bone screw. The second device in this arrangement is a passive component that in one embodiment is a slave to the first device or module.

The bone screw can then be implanted in the bone that is to be assessed, and then functions as the passive aspect of the dual mode closed-loop measurement system. A medical reader placed in close proximity to the bone screw and comprising the inductor drive circuit, functions as the active aspect of the dual mode closed-loop measurement system. The first device in this arrangement is an active component, for example, a master that provides the power and control. The medical reader can itself be an internally placed medical implant device, such as a trial insert, or an externally engaged medical device, such as a wireless energy source configured to supply power and also read (receive or process) the propagated energy waves. The bone screw embodiment is for illustration only and is not indicative of limitations on the range of embodiments for this or any other application.

In yet another embodiment, the sequence is reversed; that is, the first device actively transmits an energy wave through the propagation medium to be measured and that is received by the transducer on the second device. The transducer on the second device activates an operatively coupled inductor, which then generates a low-level electromagnetic field. This field is then in turn measured by a receive inductor on the first device. As one example, the field can be externally measured by an RFID reader or an external wireless energy source.

These embodiments illustrate the flexibility the present invention facilitates, especially, but not limited to, highly compact embodiments in a wide range of form factors. This flexibility, over a wide range of sizes and form factors, may be achieved without compromising measurement accuracy or resolution. In this example embodiment, the wireless modules are integrated into screw shaped medical devices to facilitate measurement of physical or physiologic parameters of interest. The medical devices are positioned with the contacting or sensing surfaces engaged with members of the body such that the parameter or parameters of interest affect propagation of energy waves or pulses between the medical devices.

Figure 15:
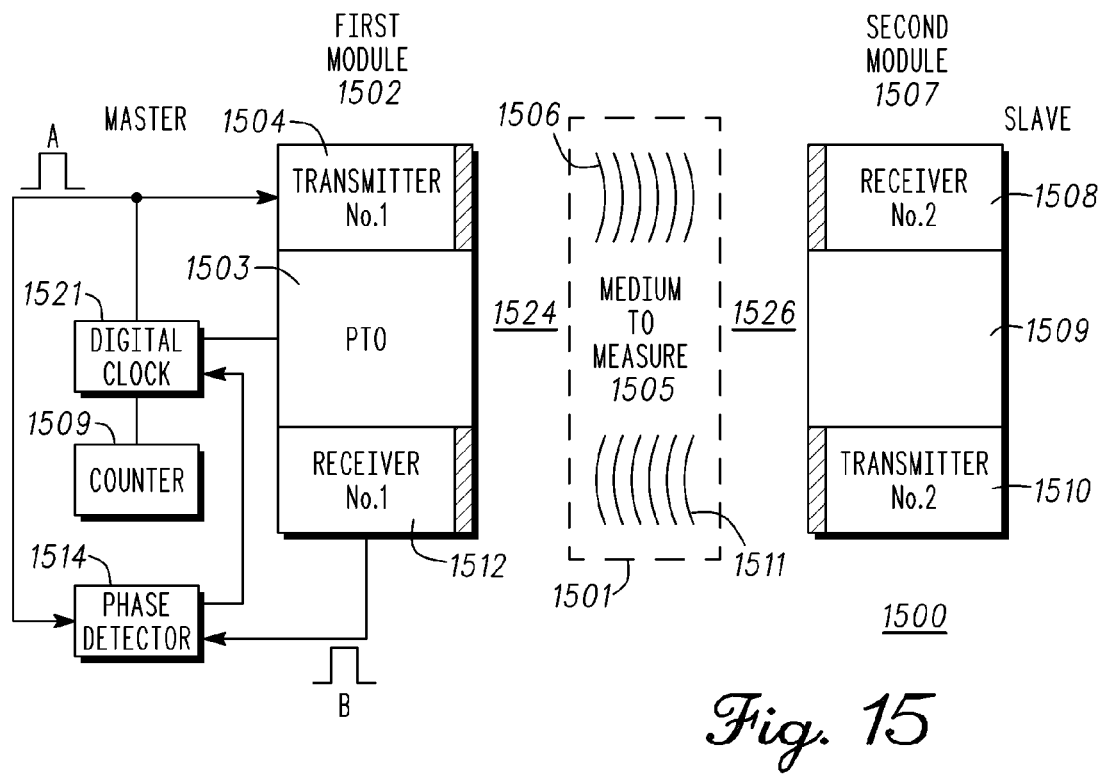
FIG. 15 is another exemplary block diagram of a dual mode closed loop measurement system in accordance with one embodiment.

FIG. 1 is a schematic diagram of a dual-mode closed loop measurement system 100 in accordance with one embodiment. System 100 comprises a first circuit A and a second circuit B. Briefly, the dual-mode closed loop measurement system 100 operates via inductive-to-inductive coupling on a first transmission coupling path and piezo-to-piezo on a second transmission coupling path. Refer ahead to FIG. 15 to review dual-mode closed loop measurement operation on a same type of transmission coupling (e.g., piezo-to-piezo).

With regard to FIG. 1, the first circuit A comprises a filter 110, a driver circuit 102, an inductor 104, a transducer 106, and a buffer circuit 108. Filter 110 has an input connected to node 124 and an output. Filter 110 can be a passive or active filter. In the example shown, filter 110 is a passive low pass filter. Driver circuit 102 has an input connected to the output of filter 110 and a differential output for driving a first and second leads of inductor 104. In at least one exemplary embodiment, inductor 104 is used for powering the system as disclosed ahead and used as a functional element of the dual-mode closed loop measurement system 100. Using inductor 104 for more than one purpose lowers cost, reduces the number of components required in the system, and minimizes the system footprint. Transducer 106 has a first lead and a second lead connected to ground. In at least one exemplary embodiment, transducer 106 is a piezo-electric transducer that operates in the ultrasonic frequency range. Buffer circuit 108 has a first input connected to the first lead of transducer 106, a second lead connected to ground, and an output connected to node 124. Other circuitry will be explained ahead for controlling system operations and transmitting/receiving information.

The second circuit B is a remote device 112 that comprises an inductor 114 and a transducer 116. In at least one exemplary embodiment, transducer 116 is a piezo-electric device that operates at ultrasonic frequencies. Remote sensor 112 is housed separately from the first circuit. In at least one exemplary embodiment, the first and second circuits can be placed in an organism either temporarily or permanently. In one embodiment, a material 122 to be monitored is bone of a human or animal, or other biological tissue or engineered material. In a non-limiting example, the first and second circuits A and B are placed in such a manner that living bone is between the circuits. This has the substantial benefit of direct monitoring of the bone, which is more accurate than monitoring from outside the body. Treatments can be monitored over time to determine effectiveness. Conditions such as osteolysis can be monitored to determine the rate of change in bone density thereby becoming aware of dangerous conditions that can be life threatening. Material 122 can be biological or non-biological. For example, dual-mode closed loop measurement system 100 can be used to monitor a glue joint in joint implant. A common failure mechanism of an implanted joint is a reduction in bond strength over time. Cracking of the glue and seepage of fluid into the cracks accelerates degradation of the bond. The status of the glue joint can be monitored by placing the first and second circuits on either side of the glue joint thereby identifying a weakening glue joint prior to failure and allowing simpler counter measures to be taken to eliminate the issue.

Figure 2:
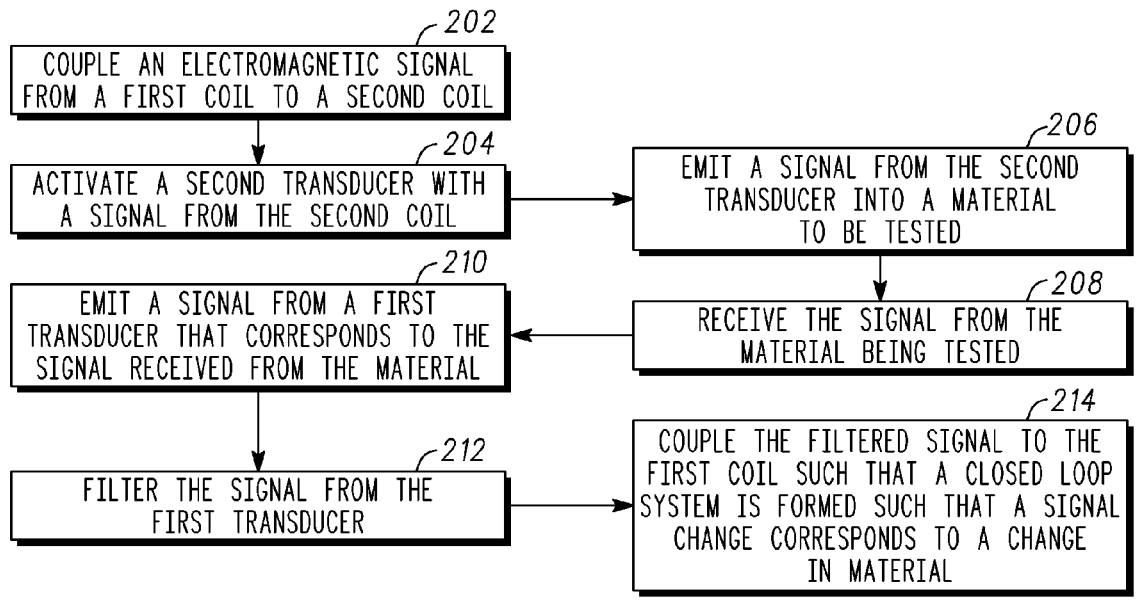
FIG. 2 is an exemplary flow chart of a method for dual mode closed loop measurement in accordance with one embodiment.

FIG. 2 is an exemplary flow chart 200 of method steps performed by dual-mode closed loop measurement system 100 for assessing material properties between the first and second circuits of the medical sensor in accordance with one embodiment. The first and second circuits form a closed loop system having a first and second path. The first path comprises inductors 104 and 114. Inductors 104 and 114 are a predetermined distance 118 from one another (or can be determined) and are electromagnetically connected, for example, analogous to a transformer. Predetermined distance 118 is determined to ensure coupling of inductors 104 and 114 while allowing changes in material 122 to be detected. In at least one exemplary embodiment, the electromagnetic field couples through material 122. A signal coupled to node 124 or provided by buffer 108 is filtered by low pass filter 110. The filtered signal is then provided to driver circuit 102, which drives inductor 104. The signal applied to inductor 4 is electromagnetically coupled to inductor 114 in a step 202.

Inductor 114 is connected to transducer 116. The signal coupled to inductor 114 is applied to transducer 116, which activates as shown in step 204. A threshold level of electrical energy can be established to stimulate the piezoelectric transducer. Transducer 116 then emits a corresponding ultrasonic signal into material 122 in a step 206. Transducer 116 is connected to material 122 to ensure transfer of the ultrasonic signal. Once transferred the ultrasonic signal propagates through material 122. The ultrasonic signal propagates the predetermined distance 120 to be received by transducer 106. In at least one exemplary embodiment, predetermined distance 120 is a known and fixed distance. Alternatively, a sensing system can be used to periodically measure the distance between transducers 106 and 116.

Transducer 106 receives the ultrasonic signal from material 122 as disclosed in step 208. In at least one exemplary embodiment, transducer 106 is a piezo-electric device that converts the ultrasonic signal to an electrical signal. Transducer 106 emits a signal that corresponds to the signal received from material 122 in a step 210. The energy loss through the closed loop comprising inductor 104, inductor 114, transducer 116, the material 122 (e.g. propagation-medium), and transducer 106 loop is such that a signal propagation through the material 122 can be sustained thereby allowing reliable measurements to be taken within the constraints of the energy storage capacity of the master/sensing module (e.g., circuits A and B). The signal from transducer 106 is received by buffer 108. Buffer 108 precisely detects a signal from transducer 106 corresponding to an energy wave propagating through the medium. Buffer 108 further generates a signal corresponding to the energy wave. In one embodiment, buffer 108 is a comparator outputting a square wave signal.

The signal from buffer 108 is filtered by low pass filter 110, for example, by filtering, as shown in step 212. Low pass filter 110 removes high frequency components of the square wave signal. The filtered signal from buffer 108 is provided back to node 124 thereby closing the signal loop. At step 214, the filtered signal is coupled to the first coil such that a closed loop system is formed and that by frequency and time analysis identifies changes in the material. The signal through the closed loop will stabilize over time. The frequency of the signal correlates to the properties of material 122. In at least one exemplary embodiment, with material 122 as bone, the frequency will correspond to bone density. Changes in bone density will modify the transit time of the signal across predetermined distance 120, which is a function of the predetermined distance 120. A direct distance measurement enhances the accuracy of the results. Closing the loop provides a stable signal that can be monitored. The system can be placed in the organism for an extended period of time where it is only powered when a measurement is desired. This also has the benefits of taking measurements periodically over an extended period of time, and offers flexibility to downsize the passive module even further.

Although components of FIG. 1 were disclosed for enabling aspects of the method, other embodiments are herein contemplated, for example, a single master/sensing module that queries two or more passive modules, incorporating aspects of Radio Frequency Identification (RFID). In this configuration, a single implanted active can multiplex (mux) multiple very small passive modules the same way individual sensing assemblages are multiplexed within the existing sensing module, as will be explained ahead. This may permit applications for 360-degree-like viewing. As will also be explained ahead, a propagation tuned oscillator operating in continuous mode, pulse loop, or pulse echo mode is extended for operation as a dual-mode closed-loop measurement system.

FIG. 3 is an exemplary illustration for screw sensor construction via flex rolling or die stacking in accordance with one embodiment. One or more electrical components 332 correspond to the second circuit B of FIG. 1. Electrical components 332 can be integrated circuits, ASICs, or passive components. The electrical components are 332 can be affixed to and electrically coupled in a circuit configuration on substrate 331. In a non-limiting example, substrate 331 can be a flex-cable, ribbon, flexible printed circuit board, or other medium that can be placed in a compact form and provides electrical interconnect for electrical components. The substrate 331 can be altered from a planar shape to achieve a small form factor. For example, substrate 331 can be folded or rolled up to achieve a form factor 333. In one embodiment, inductor 114 and transducer 116 is formed on or mounted to substrate 331 and coupled as shown in FIG. 1 as a passive circuit.

FIG. 4 is an exemplary illustration of a screw sensor 335 construction via flex rolling or die stacking insertion in accordance with one embodiment. Screw sensor 335 includes a cavity 337 for receiving substrate 331. The substrate 331 in the small form factor 333 is inserted in the cavity 337 of the orthopedic screw in the direction shown. Referring back to FIG. 3, an alternate embodiment stacks the electrical components 334 of the second circuit B of FIG. 1. The stacked die in small form factor 333 is similarly inserted in a hollow or cavity of the orthopedic screw 335 shown in FIG. 4. A combination of these two approaches can also be performed to construct the orthopedic screw 335.

The sharpness of the bends in the flex substrate 331 can be assessed in-situ to ensure that they do not compromise the integrity of the electrical traces or interconnect. In one embodiment, the substrate is between the interconnect and the walls of the cavity. The stacked die approach provides the benefit of minimizing the Z-dimension. The stack height can be controlled to ensure the proper form factor 333 for a corresponding housing. The stacked die approach can also minimize the footprint to the largest single package of die and chip-style discrete components as well as the complexity of the flex substrate by optimizing the number of packages versus their individual footprints that must be attached to the flex.

A screw gun is a common tool used by orthopedic surgeons. Similarly, screws are commonly used in orthopedic surgeries to fasten elements together. Surgeons will have such familiarity with orthopedic screw 335 that an adoption cycle to using the passive circuit coupled therein will be rapid. Screw 335 is made of bio-compatible materials that can remain in the human body indefinitely. Moreover, screw 335 can be directed very accurately in to a predetermined position.

FIG. 5 is an illustrative embodiment of a sensor 306 as used in the dual mode closed loop measurement system in accordance with one embodiment. The measurement system comprises an active sensor 302 and a passive sensor 306. Active sensor 302 and passive sensor 306 respectively correspond to the first circuit A and the second circuit B of FIG. 1. Passive sensor 306 corresponds to screw sensor 335 described in FIG. 4. Sensor 302 can have components similar to that of a sensing module disclosed hereinbelow in FIG. 10.

In a non-limiting example sensor 302 is coupled to a surface 308 corresponding to a first location of a medium. A transducer of sensor 302 is coupled to surface 308. In an example of measuring bone density, the medium is bone 304. Similarly, screw 306 is screwed into a second location of the medium such as bone 304. A transducer of sensor 306 couples through the body of the screw to the second location. Sensor 302 and sensor 306 form a close-loop that respectively comprises a first module and a second module in communication with each other. The communication between the first and second modules includes a first path and a second path. As disclosed herein the first and second path can use a same signal type. Alternatively, the first and second paths can have different signal types. In one embodiment, the first path comprises an electromagnetic or inductive coupling between inductors of sensor 302 and sensor 306. A second path comprises an acoustic path from the first location to the second location of bone 304. The second path is coupled by an energy wave propagating between the first and second location of bone 304. In one embodiment, the energy wave is an ultrasonic energy wave or pulse. Sensor 306 is a passive circuit. The transducer of sensor 306 is energized by electromagnetic energy received by the inductor of sensor 306 from the inductor of sensor 302.

Operation of the parameter measurement system is disclosed below. The first module or sensor 302 sends an electromagnetic signal to the second module or sensor 306. The inductors of the first and second modules can be inductively coupled together similar to a transformer for efficient transfer of the signal. Sensor 302 is a passive circuit and the electromagnetic signal received by the inductor of sensor 306 powers the transducer of sensor 306 to emit one or more energy waves at the second location into bone 304. In the example, sensor 306 is screwed into bone 304. The screw to bone interface is a good conductor of an energy wave. The emission of the energy wave can be directional or non-directional from sensor 306. In general, the one or more energy waves propagate towards the interface 308. The one or more energy waves propagate to interface 308 where they are detected by sensor 302. Sensor 302 measures at least one of transit time, frequency, or phase corresponding to the propagation of an energy wave across a predetermined distance from the first location to the second location of bone 304. Closing the loop comprising the first path and the second path forms a propagation tuned oscillator (PTO). The propagation tuned oscillator and more particularly sensor 302, upon detecting a propagated energy wave at the first location generates an electromagnetic signal that couples from the inductor of sensor 302 to the inductor of sensor 306 thereby initiating the emission of a new energy wave. The positive closed-loop feedback of the parameter measurement system sustains the emission, propagation, detection, and measurement of the propagated energy waves. The transit time, frequency, or phase of the measured propagated energy waves can be related to material properties of the propagating medium. In the example, the transit time, frequency, or phase of an energy wave propagating through bone has a known relationship to bone density which is then calculated from the measurements.

FIG. 6 is an illustrative embodiment of the screw sensor 306 as used in the dual mode closed loop measurement system in accordance with one embodiment. In this example, the energy wave propagation path differs from the path that is perpendicular to the insert direction as shown in FIG. 5 but operates similarly to that described above. The sensor 306 is inserted by rotation inside bone 304. The active sensor 302 is coupled to a bone interface above a head of sensor 306. The propagation path of an energy wave for detection is aligned in a direction of the insertion path of sensor 306. In one embodiment, energy waves are emitted from sensor 306 and propagate a distance 310 through bone 304 to active sensor 302. Thus, sensor 306 can be used to propagate energy waves in more than one direction or energy waves can be received at multiple location points on the bone to measure transit times for different paths.

Figure 7:
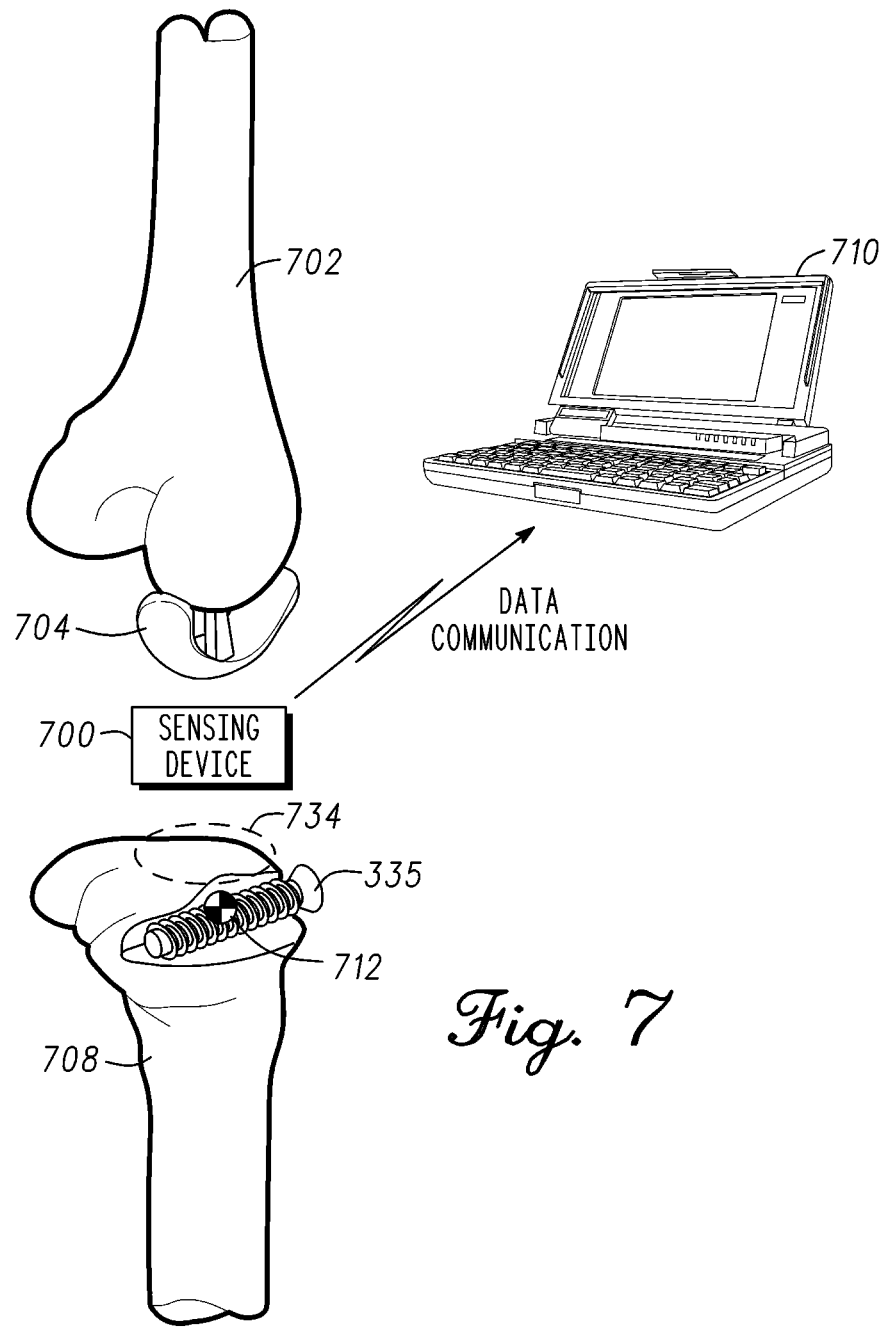
FIG. 7 is an exemplary illustration of a medical sensing system with the screw sensor operating in accordance the dual mode closed loop sensing in accordance with one embodiment.

FIG. 7 is an exemplary illustration of a medical sensing system with the screw sensor 335 operating in accordance the dual mode closed loop sensing in accordance with one embodiment. Screw sensor 335 illustrates a medical sensing system operating in accordance the dual mode closed loop sensing. As shown, the dual mode closed loop sensing system and more specifically the second circuit B in this embodiment comprises the bone screw 335. The bone screw 335 includes inductor 114 and 116 on a flexible interconnect coupled together as shown in FIG. 1. The sensing device 700 serves as the active device (e.g., master) providing power to the electronic components and operative control. The bone screw 335 with the embedded electronic components serves as the passive device 712 (e.g., slave). Although the illustration shows the top of the bone screw as protruding, this is for illustration and it may be completely embedded in the bone. In one embodiment, an inductor and coil of the first circuit A of FIG. 1 is located in a region 302. The inductor and coil of the first circuit A and the bone screw 335 bounds a bone region 304 such that the devices are spaced a distance 310 apart from one another. The bone screw 335 is inserted in a region 306 into the bone using common orthopedic surgical techniques. The threads of screw 335 engage with the bone and firmly hold the device in place either temporarily or permanently. In the example, the system measures and monitors changes to bone density. Between the sensing device 700 and the bone screw 335 is the bone region 734 that is measured by the system, for example, to determine bone density. As will be explained ahead in further detail, the medical sensing system measures the characteristics of the energy waves propagating through the bone region 734, namely, transit time and associated parameters of frequency, amplitude and phase to determine the parameters of interest. This data can be conveyed to a receiver station 710 via wireless for processing and display.

In one embodiment, the medical sensing system comprises an active system with transmit/receive sensing, the material to be measured, and a passive component with receive/transmit sensing. The material to be measured is between the active system and the passive component. As shown, the material is perpendicular to the insertion path of the passive component but can other orientations. The passive components are housed in a screw common for orthopedic use. The material spacing between the active system and the passive component is of a known or predetermined distance. The transmit path is through electromagnetic coupling from inductor to inductor. The electromagnetic field couples through or around the material. The receive path is acoustic ultrasonic energy waves coupling piezo-electric transducer to piezo-electric transducer. A benefit of dual mode sensing is that the transmit inductor to inductor coupling is very energy efficient enabling low power applications or temporary powering of the system to take measurements. The material properties, for example bone density, is determined by analyzing the signal transferred or propagated through the material and differential measurements of how the signal changes over time.

Figure 8:
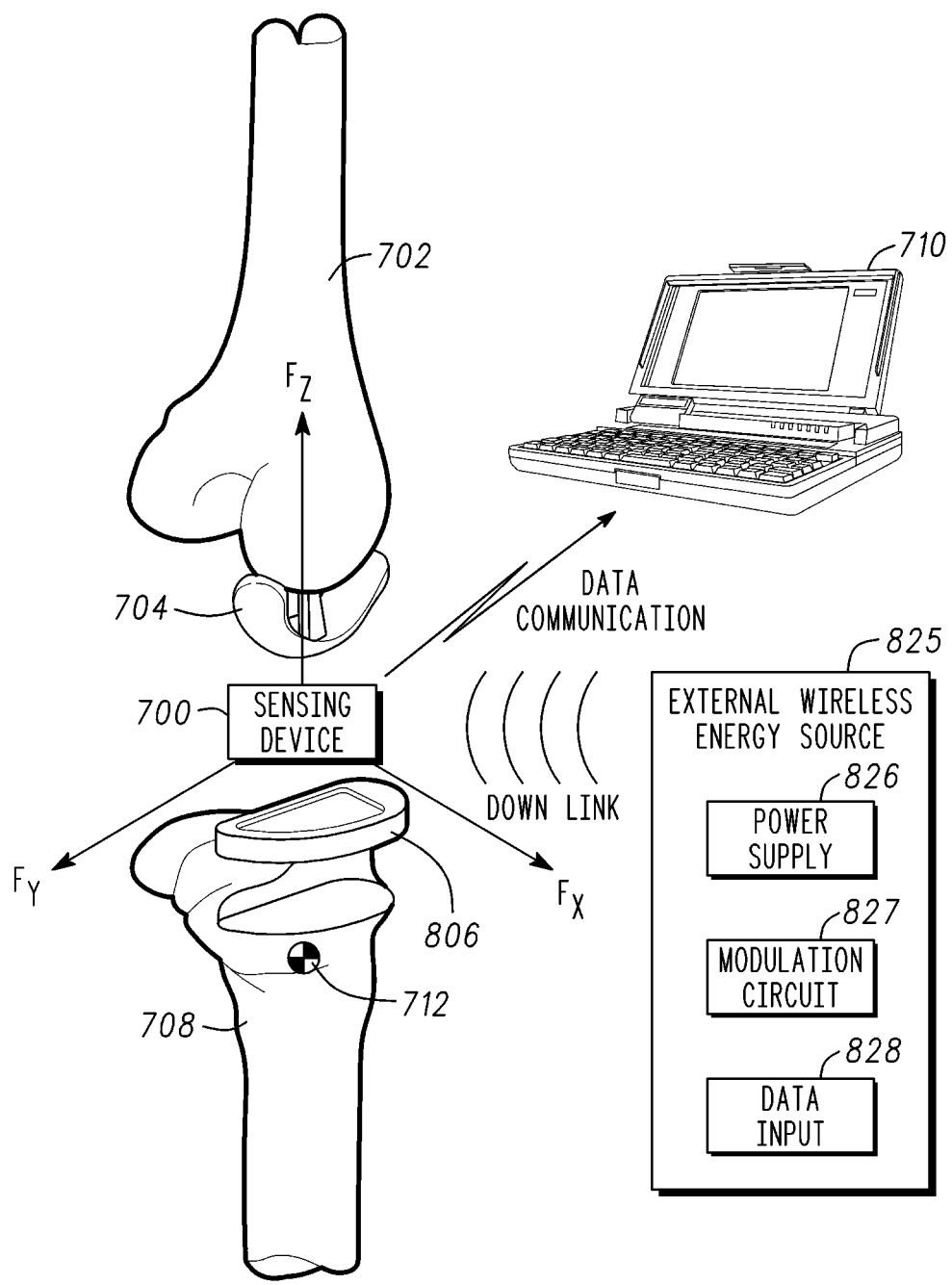
FIG. 8 is an exemplary illustration of a medical sensing system operating in accordance the dual mode closed loop sensing in accordance with one embodiment.

FIG. 8 is an exemplary illustration of a medical sensing system operating in accordance the dual mode closed loop sensing in accordance with one embodiment. An external wireless energy source 825 can be placed in proximity to the sensing device 700 to provide wireless power to recharge a power source that enables operation. As an example, the external wireless energy source 825 generates energy transmissions that are wirelessly directed to the medical sensing device 700 and received as energy waves via resonant inductive coupling. The external wireless energy source 825 can modulate a power signal generating the energy transmissions to convey down-link data, which is then demodulated from the energy waves at the medical sensing device 700. As one example, the medical sensing device 700 is a load sensor insert device 700 suitable for use in knee joint replacement surgery. It can intra-operatively assess a load on the prosthetic knee components (implant) and collect load data for real-time viewing of the load, for example, over various applied loads and angles of flexion. The external wireless energy source 825 can be used to power the load sensor insert device 700 during the surgical procedure or thereafter when the surgery is complete and the load sensor insert device 700 is implanted for long-term use.

In a second example, sensing device 700 measures material properties and changes in material properties over time. The material to be monitored is placed between sensing device 700 and a component 712, for example, part of a bone screw in accordance with embodiments herein. As shown, the sensor of sensing device 700 is coupled to the tibia. Component 712 is inserted in the bone of the tibia in proximity to the sensor of sensing device 700. Bone material of the tibia is between sensing device 700 and component 712. Component 712 includes circuitry that is in communication with sensing device 700. In at least one exemplary embodiment, component 712 is formed as a screw that can be inserted into the tibia at a predetermined location. A screw is a common component used in orthopedic surgery and will require little training to use. The closed loop system comprises sensing device 700, a portion of the tibia (material being sensed), and component 712.

In one system embodiment, the load sensor insert device 700 transmits measured load data to a receiver 710 via one-way data communication over the up-link channel for permitting visualization of the level and distribution of load at various points on the prosthetic components. This, combined with cyclic redundancy check error checking, provides high security and protection against any form of unauthorized or accidental interference with a minimum of added circuitry and components. This can aid the surgeon in making any adjustments needed to achieve optimal joint balancing. In addition to transmitting one-way data, communications can occur over the up-link channel to the receiver station 710. The load sensor insert device 700 can receive down-link data from the external wireless energy source 825 during the wireless power recharging operation. The down-link data can include component information, such as a serial number, or control information, for controlling operation of the load sensor insert device 700. This data can then be uploaded to the receiving system 710 upon request via the one-way up-link channel, in effect providing two-way data communications over separate channels.

As shown, the wireless energy source 127 can include a power supply 826, a modulation circuit 827, and a data input 828. The power supply 826 can be a battery, a charging device, a power connection, or other energy source for generating wireless power signals to charge the load sensor insert device 700. The external wireless energy source can transmit energy in the form of, but not limited to, electromagnetic induction, or other electromagnetic or ultrasound emissions. The data input 828 can be a user interface component (e.g., keyboard, keypad, touchscreen) that receives input information (e.g., serial number, control codes) to be downloaded to the load sensor insert device 700. The data input 828 can also be an interface or port to receive the input information from another data source, such as from a computer via a wired or wireless connection (e.g., USB, IEEE802.16, etc.). The modulation circuitry 827 can modulate the input information onto the power signals generated by the power supply 826.

During a knee procedure, the surgeon can affix a femoral prosthetic component 704 to the femur 702 and a tibial prosthetic component 806 to the patient's tibia 708. The tibial prosthetic component 706 can be a tray or plate affixed to a planarized proximal end of the tibia 708. The sensing device 700 is a load sensing insert that is fitted between the plate of the tibial prosthetic component 706 and the femoral prosthetic component 704. These three prosthetic components (704, 700 and 806) enable the prostheses to emulate the functioning of a natural knee joint.

The sensing device 700 can be a mechanical replica of a final tibial implant. It can measure loads at various points (or locations) on the femoral prosthetic component 704 and transmit the measured data to a receiving station 710 by way of a loop antenna. The receiving station 710 can include data processing, storage, or display, or combination thereof and provide real time graphical representation of the level and distribution of the load.

As one example, the sensing device 700 can measure forces (Fx, Fy, Fz) with corresponding locations on the femoral prosthetic component 704 and the tibial prosthetic component 806. It can then transmit this data to the receiving station 710 to provide real-time visualization for assisting the surgeon in identifying any adjustments needed to achieve optimal joint balancing.

In the second example, a closed loop signal has a path through a portion of the bone of the tibia. The closed loop signal will correlate to material properties such as bone density. Thus, changes in bone density can be monitored and preventative actions taken when the conditions warrant concern. Furthermore, monitoring can provide valuable information on how effective the treatments are. The system can be temporary or permanent.

Figure 9:
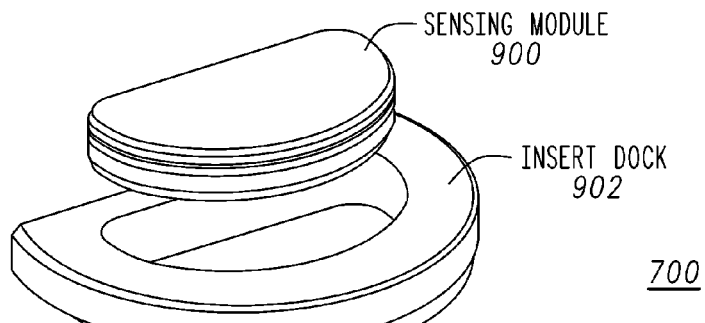
FIG. 9 is a perspective view of the medical sensing device in accordance with one embodiment.

FIG. 9 is a perspective view of the medical sensing device 700 in accordance with one embodiment. As illustrated, the sensing device 700 can include a sensing module 900 and an insert 702. The sensing module 700 can securely fit within the insert dock 702. The insert dock 702 can securely attach or slide onto the tibial prosthetic component 806 of FIG. 8. The prosthetic components of FIG. 8 can be manually coupled prior to surgical placement or during the surgery. The sensing module 700 in other embodiments (without the insert dock 702) can affix directly to load bearing surfaces exposed to forces, for example, forces applied upon a load bearing component during flexion of the joint. Although illustrated as separate, in yet another embodiment, the sensing module 700 and insert dock 702 can be combined together as an integrated sensing module.

The sensing module 700 is an encapsulating enclosure with a unitary main body and load bearing contact surfaces that can be, but are not limited to, dissimilar materials, combined to form a hermetic module or device. The components of the encapsulating enclosure may also consist of, but are not limited to, bio-compatible materials. For medical applications, the encapsulating enclosure may be required to be hermetic. The encapsulating enclosure can comprise biocompatible materials, for example, but not limited to, polycarbonate, steel, silicon, neoprene, and similar materials.

The range of nonmedical and medical applications for the sensing device is extensive. Requirements of individual applications of wireless modules or devices drive the selection of the power source and architecture, the form of energy and transducers coupled to the medium of propagation, as well as the form of energy and transducers for inter-module or inter-device communication. One factor driving the selection of the forms of energy and energy transducers is the mode of measurement operation that fits each application and parameter or parameters of interest within the body or physical system being studied. The modes of measurement may include, but are not limited to, short-term, temporary measurement, point-in-time measurement, and continuous measurement. Up to four separate forms or frequencies of energy may be used by pairs of wireless modules or devices during charging, measuring, and communication operations. These include energy for powering each wireless module or device, energy waves or pulses coupled through the propagating medium within the body or physical system, energy pulses for inter-module wireless module or device communication, and energy waves for telemetry communication of measurement data to external instruments or equipment. For example, but not limited to, electromagnetic induction that is used for charging the energy storage device within each wireless module or device, ultrasonic waves or pulses may be propagated through the propagation medium, low frequency RF pulses may be used for inter-module or inter-device communication enabling closed-loop measurement, and higher frequency RF emissions may be used for telemetry to communicate measurement data to external instruments or devices. Obviously, there are many other possible combinations and permutations, including, but not limited to, the use of optical transducers or lasers and light or infrared energy waves or pulses. For modes of measurement that charge the internal power supply before beginning measurement operation only three distinct forms or frequencies of energy may be required during measurement and data reporting operations.

Figure 10:
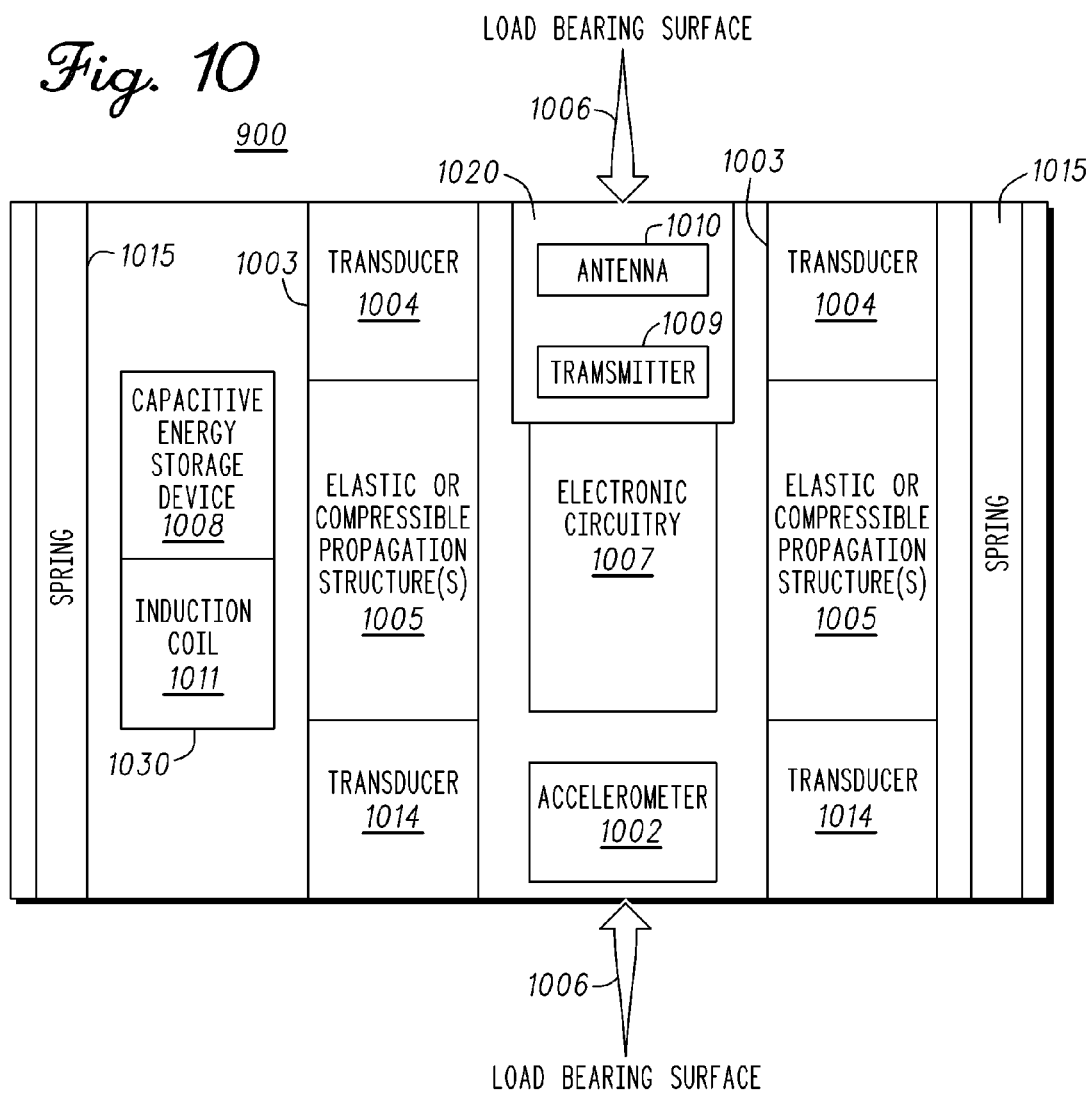
FIG. 10 is a block model diagram of the sensing module in accordance with one embodiment.

FIG. 10 is a block model diagram of the sensing module 900 in accordance with one embodiment. It should be noted that the sensing module 900 can comprise more or less than the number of components shown. As illustrated, the sensing module 900 includes one or more sensing assemblages 1003, a transceiver 1020, an energy storage 1030, electronic circuitry 1007, one or more mechanical supports 1015 (e.g., springs), and an accelerometer 1002.

The sensing assemblage 1003 can be positioned, engaged, attached, or affixed to the load bearing contact surfaces 1006. Mechanical supports 1015 serve to provide proper balancing of load bearing contact surfaces 1006. Load bearing surfaces 1006 can move and tilt with changes in applied load; actions which can be transferred to the sensing assemblages 1003 and measured by the electronic circuitry 1007. The electronic circuitry 1007 measures physical changes in the sensing assemblage 1003 to determine parameters of interest; for example, a level, distribution and direction of forces acting on the load bearing contact surfaces 1006. Power for the sensing module 900 is provided by the energy storage 1030.

As one example, the sensing assemblage 1003 can comprise an elastic or compressible propagation structure 1005 between a first transducer 1004 and a second transducer 1014. In the current example, the transducers can be an ultrasound (or ultrasonic) resonator, and the elastic or compressible propagation structure 1005 can be an ultrasound (or ultrasonic) waveguide (or waveguides). The electronic circuitry 1007 is electrically coupled to the sensing assemblages 1003 and translates changes in the length (or compression or extension) of the sensing assemblages 1003 to parameters of interest, such as force. It measures a change in the length of the propagation structure 1005 (e.g., waveguide) responsive to an applied force and converts this change into electrical signals which can be transmitted via the transceiver 1020 to convey a level and a direction of the applied force. In other arrangements herein contemplated, the sensing assemblage 1003 may require only a single transducer. In yet other arrangements, the sensing assemblage 1003 can include piezoelectric, capacitive, optical or temperature sensors or transducers to measure the compression or displacement. It is not limited to ultrasonic transducers and waveguides.

The accelerometer 1002 can measure acceleration and static gravitational pull. It can include single-axis and multi-axis structures to detect magnitude and direction of the acceleration as a vector quantity, and can be used to sense orientation, vibration, impact and shock. The electronic circuitry 1007 in conjunction with the accelerometer 1002 and sensing assemblies 1003 can measure parameters of interest (e.g., distributions of load, force, pressure, displacement, movement, rotation, torque and acceleration) relative to orientations of the sensing module 900 with respect to a reference point. In such an arrangement, spatial distributions of the measured parameters relative to a chosen frame of reference can be computed and presented for real-time display.

The transceiver 1020 can include a transmitter 1009 and an antenna 1010 to permit wireless operation and telemetry functions. In various embodiments, the antenna 1010 can be configured by design as an integrated loop antenna. The integrated loop antenna can be configured at various layers and locations on the electronic substrate with electrical components and by way of electronic control circuitry to conduct efficiently at low power levels. Once initiated the transceiver 1020 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module 900 with a power source or control circuitry or with associated data collection, storage, or display equipment.

The transceiver 1020 receives power from the energy storage 1030 and can operate at low-power over various radio frequencies by way of efficient power management schemes, for example, incorporated within the electronic circuitry 1007. As one example, the transceiver 1020 can transmit data at selected frequencies in a chosen mode of emission by way of the antenna 1010. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

Briefly, antenna 1010 can be integrated with components of the sensing module 900 to provide the radio frequency transmission. The substrate for the antenna 1010 and electrical connections with the electronic circuitry 1007 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

Minimizing circuitry or antenna for downlink telemetry can enable the construction of, but not limited to, highly compact wireless devices for a wide range of non-medical and medical applications. Examples of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

The energy storage 1030 provides power to electronic components of the sensing module 900. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 1030, the sensing module 900 can be operated with a single charge until the internal energy is drained. It can be recharged periodically to enable continuous operation. For compact electronic modules or devices, ultra-capacitors or super capacitors, or other form of capacitors provide many benefits over other rechargeable technologies.

The energy storage 1030 can utilize common power management technologies such as replaceable batteries, supply regulation technologies, and charging system technologies for supplying energy to the components of the sensing module 900 to facilitate wireless applications. The energy storage 1030 minimizes additional sources of energy radiation required to power the sensing module 900 during measurement operations. In one embodiment, as illustrated, the energy storage 1030 can include a capacitive energy storage device 1008 and an induction coil 1011. External source of charging power can be coupled wirelessly to the capacitive energy storage device 1008 through the electromagnetic induction coil or coils 1011 by way of inductive charging. The charging operation can be controlled by power management systems designed into, or with, the electronic circuitry 1007. As one example, during operation of electronic circuitry 1007, power can be transferred from capacitive energy storage device 1008 by way of efficient step-up and step-down voltage conversion circuitry. This conserves operating power of circuit blocks at a minimum voltage level to support the required level of performance.

As previously noted, in one configuration, the energy store 1030 can communicate downlink data to the transceiver 1020 during a recharging operation. For instance, downlink control data can be modulated onto the energy source signal and thereafter demodulated from the induction coil 1011 by way of electronic control circuitry 1007. This can serve as a more efficient way for receiving downlink data instead of configuring the transceiver 1020 for both uplink and downlink operation. As one example, downlink data can include updated control parameters that the sensing module 900 uses when making a measurement, such as external positional information, or for recalibration purposes, such as spring biasing. It can also be used to download a serial number or other identification data.

The electronic circuitry 1007 manages and controls various operations of the components of the sensing module 900, such as load sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 1007 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), or a Micro-Controller (μC), with associated storage memory and logic. The controller can utilize computing technologies with associated storage memory such a Flash, ROM, RAM, SRAM, DRAM or other like technologies for controlling operations of the aforementioned components of the sensing module 900. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

Figure 11:
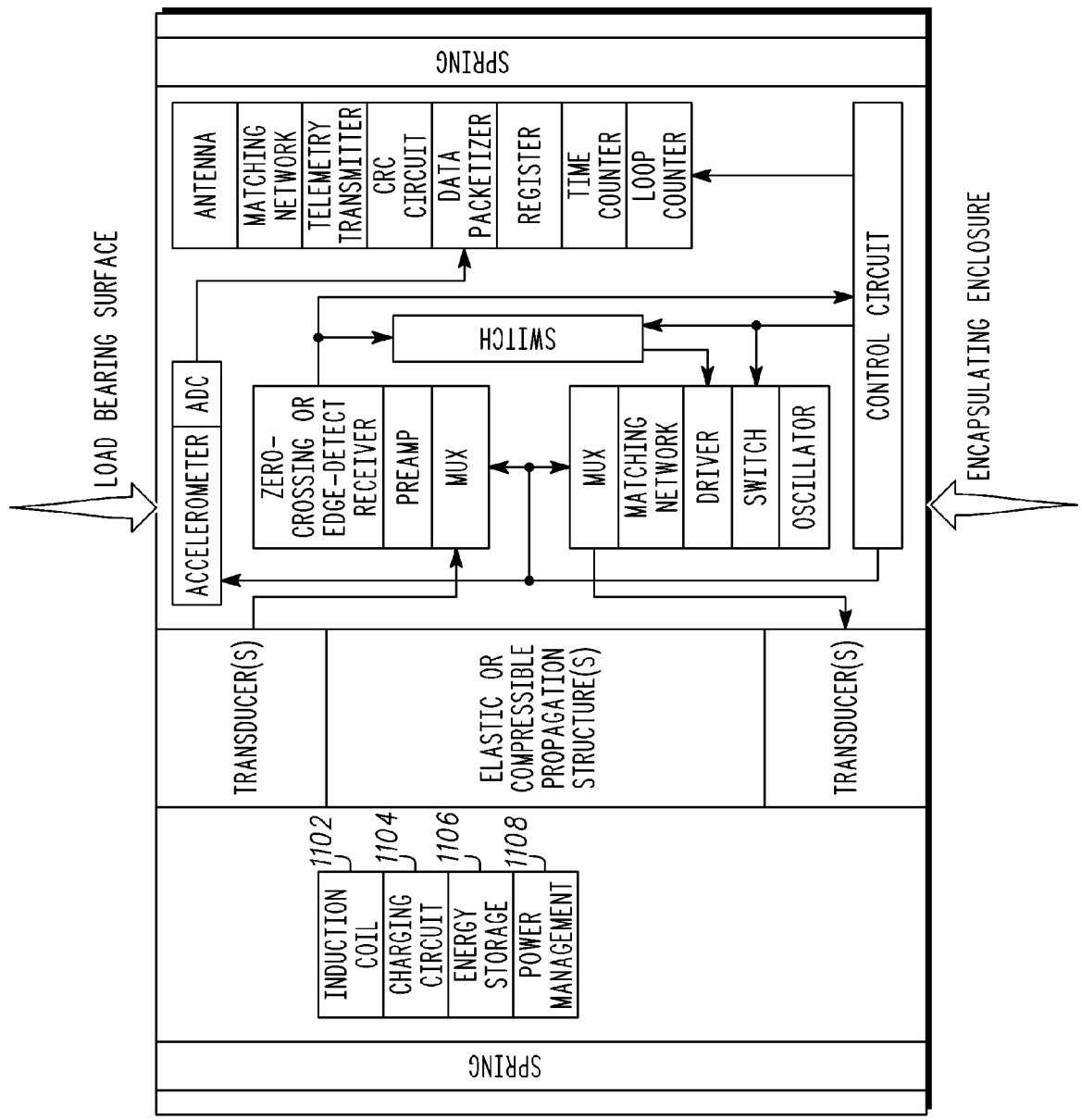
FIG. 11 is a more detailed block model diagram of the sensing module in accordance with one embodiment.

FIG. 11 is a more detailed block model diagram of the sensing module 900 in accordance with one embodiment. The diagram depicts in one embodiment a block diagram 1100 of the sensing module 900 where certain components are replaced or supplemented with specialized ASICs. As illustrated, the charging circuit 1104 can be an integrated circuit operatively coupled to the inductor coil 1102 for charging the energy store 1106. Inductor coil 1102 can also be used in a sensing operation as described hereinabove. The power management circuitry 1108 can manage wired and wireless charging operations for operating the sensing module 1100. As another example, electronic circuitry 1007 is supplemented with a matching network, zero-crossing or edge detect receiver, and propagation tuned oscillator to precisely track transit time of ultrasound waves in the elastic or compressible propagation structures. Integration of the telemetry transmitter and sensor modules enables construction of a wide range of sizes of the sensing module 1100. This facilitates capturing data, measuring parameters of interest and digitizing that data, and subsequently communicating that data to external equipment with minimal disturbance to the operation of the body, instrument, appliance, vehicle, equipment, or physical system for a wide range of applications. Moreover, the level of accuracy and resolution achieved by the total integration of communication components, transducers, waveguides, and oscillators to control the operating frequency of the ultrasound transducers enables the compact, self-contained measurement module construction.

The energy storage 1106 and power management 1108 sections are responsible for powering components of the sensing module 1100. The low-power energy storage 1106 is self-powered using capacitors, ultra capacitors, super capacitors, or other forms of capacitors. Charge can be applied to the selected energy storage device 1106 through electromagnetic induction, radio frequency induction, photocells, thermocouples, ultrasound transducers, or temporary connection to batteries external power supplies. The embedded energy storage 1106 minimizes additional sources of energy radiation (to provide power for the wireless load sensing module or device) within the operating room during the implant procedure. Capacitors, ultra capacitors, or super-capacitors for energy storage enable high levels of miniaturization. Wireless charging as well as wirelessly transferring measurement data eliminates distortion of measurements caused by physical interference with movement, instruments, and standard surgical procedures during the implant procedure.

Benefits of ultra capacitors, super capacitors, or other form of capacitors as a power source instead or, or in conjunction with, other power sources or rechargeable technologies include, but are not limited to, enabling a high level of miniaturization as ultra capacitors or super capacitors are smaller than smallest available battery for the same level of energy and power for many low power applications or applications that require power only intermittently or as a short-term backup for other power sources.

For applications that require power only intermittently, ultra capacitors, super capacitors, or other form of capacitors enable rapid recharge, much faster than battery technologies and rechargeable chemistries, regardless of their energy capacity. A charge time of a capacitively powered system from a completely uncharged state can be achieved in a short period of time (minutes) because no chemical processes are involved in charging capacitors. This may be compared to charge times on the order of hours for battery technologies that typically do not charge at a rate faster than one-half the energy storage capacity of the battery within one hour. In practice, many battery applications charge at a much slower rate. Ultra capacitors, super capacitors, or other form of capacitors have almost indefinite lifetimes. There is no deterioration of a capacitor's storage capacity when uncharged, regardless of length of time at zero charge. Overcharging capacitors may pose less risk to electronics within an electronic module or device than overcharging batteries might pose. In addition, ultra capacitors, super capacitors, or other forms of capacitors eliminate storage and disposal limitations of batteries with no risk of chemical leakage. Furthermore, ultra capacitors, super capacitors, or other form of capacitors may be surface-mountable and integrate well into the electronics assemblies and standard surface-mount electronic assembly processes.

Use of ultra capacitors, super capacitors, or other form of capacitors to provide operating power for wireless devices, telemetry devices, or medical devices provides design, construction, and operating flexibility over a wide range of potential applications. Ultra-capacitors, ultra capacitors, or super capacitors, or other form of capacitors may be charged by connecting them to other power sources such as, but not limited to, a battery or batteries, an alternating current (AC) power supply, a radio frequency (RF) receiver, electromagnetic induction coil or coils, photoelectric cell or cells, thermocouple or thermocouples, or an ultrasound transducer or transducers. For compact electronic modules or devices, ultra-capacitors, ultra capacitors, or super capacitors, or other form of capacitors provide many benefits over other rechargeable technologies.

Applications may include, but are not limited to, disposable modules or devices as well as reusable modules or devices and modules or devices for long term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 12:
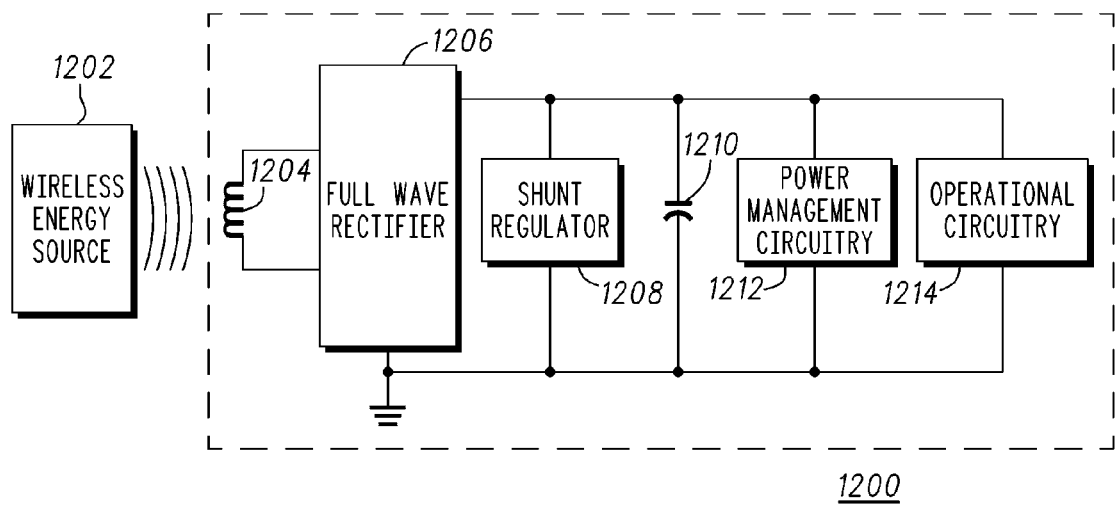
FIG. 12 is an exemplary block diagram schematic of a compact low-power energy source integrated into an exemplary electronic assembly of the medical sensing device in accordance with one embodiment.

FIG. 12 is an exemplary block diagram schematic of a compact low-power energy source 1200 integrated into an exemplary electronic assembly of the medical sensing device in accordance with one embodiment. The schematic illustrates one embodiment of the capacitive energy storage 1200 having an induction coupling to an external power source 1202 to transfer energy to a super capacitor as an energy storage device operating power for an electronic module or device. The compact low-power energy source 1200 can comprise an induction coil 1204, a rectifier 1206, a regulator 1208, a capacitive energy storage device 1210, a power management circuit 1212, and operating circuitry 1214. The latter circuits can be analog or discrete components, assembled in part or whole with other electronic circuitry, custom designed as an ASIC, or any combination thereof.

The external energy source 1202 can be coupled to a battery or batteries or an alternating current power supply. For example, external energy source 1202 can be an external hand-held device with its own battery that wirelessly transfers charge from the battery of the hand-held device to the energy source 1200 of the sensing device. The surgeon or technician can hold the hand-held device in close proximity to the sensing device prior to or during orthopedic surgery to provide sufficient charge to operate the device during the procedure. The sensing device as a long-term implant can be charged by the patient at his or her own convenience to initiate a measurement process that provides information on the implant status. In other embodiments, the sensing device being powered by charge from external energy source 1202 can communicate a signal to indicate a recharging operation is necessary, for example, when in the proximity of a charging device.

External energy source 1202 can be coupled wirelessly to capacitive energy storage device 1210 through electromagnetic induction coil or coils 1204, rectifier 1206 and regulator 1208. The charging operation is controlled by power management circuitry 1212. During operation of operating circuitry 1214, power is transferred from capacitive energy storage device 1210 by power management circuitry 1212 that includes, but is not limited to, efficient step-up and step-down voltage converter circuitry that conserves operating power of circuit blocks at the minimum voltage levels that support the required level of performance. Clock frequencies are also optimized for performance, power, and size to assure digital circuit blocks operate at the optimum clock rates that support the required level of performance. Circuit components are partitioned among integrated circuits and discrete components to also minimize power consumption without compromising performance. Partitioning functions between digital and analog circuit also enhances design flexibility and facilitates minimizing power consumption without sacrificing functionality or performance.

Figure 13:
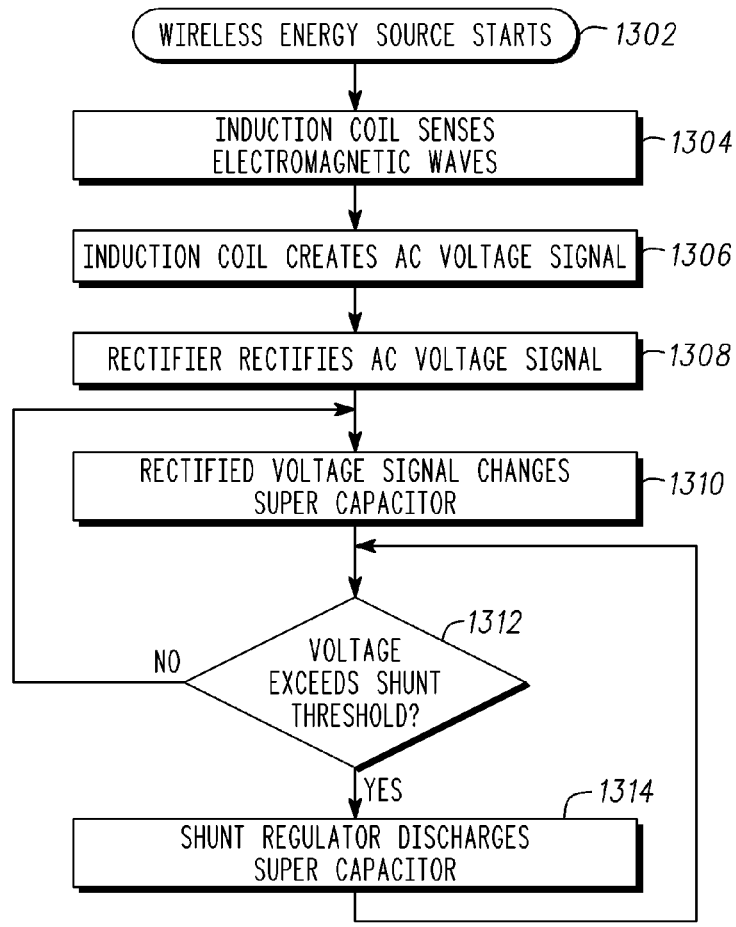
FIG. 13 is an exemplary flow chart of steps performed by the compact low-power energy source for recharging and operation of the medical sensing device in accordance with one embodiment.

FIG. 13 is an exemplary flow chart of steps performed by the compact low-power energy source 1200 for recharging and operation of the medical sensing device in accordance with one embodiment. The method 1300 can be practiced with more or less than the number of steps shown and is not limited to the order shown. To describe the method 1300, reference will be made to the components of other figures described hereinabove although it is understood that the method 1300 can be implemented in any other manner using other suitable components. The sensing module 900 described in FIG. 9 including capacitive energy storage capability and highly efficient, low power operating performance can be used to illustrate the operating principles of method 1300. The method 1300 is initiated when the external power source 1202 begins transmitting power within range of the induction coil or coils 1204 of the sensing module 900 in a step 1302. In a step 1304, the induction coils 1204 are coupled to the electromagnetic waves such that the electromagnetic waves are sensed. The induction coil or coils 1204 are energized by the power transmissions from external power source 1202. In a step 1306, the coupled electromagnetic waves creates an AC voltage signal in induction coil or coils 1204. In a step 1308, the rectifier 1206 rectifies the AC voltage signal to produce a rectified voltage signal. In one embodiment, the voltage level across induction coil or coils 1204 rises to a level that a rectified signal is generated by full-wave rectifier 1206. In a step 1310, the rectified voltage signal is used to charge the capacitive energy storage device 1210, which holds the charge. In a non-limiting example, the energy storage device 1210 is a supercapacitor having a small form factor having enough storage capability to power the sensing module 900 for a predetermined period of time. In steps 1310 and 1312, voltage regulator 1208 ensures that the capacitive energy storage device 1210 is charged to, and maintains a voltage level that is greater than the required operating voltage of the sensing module 900. Power management circuitry 1212 monitors the level of charge on capacitive energy storage device 1210 in step 1312 to determine if the voltage exceeds a threshold. The threshold can correspond to a shunt threshold established by the regulator 1208. The operating electronics circuitry 1214 is enabled when it is determined in decision block 1312 that an adequate level of charge has been stored to power the system for at least the predetermined time period.

In a step 1314, the power management circuitry 1212 disconnects the energy storage device 1210 from the charging circuitry (1204, 1206, and 1208) when the coupling with external power source 1202 is removed or terminated. Power management circuitry 1212 continues to monitor the level of charge on capacitive energy storage device 1210. The power management circuitry 1212 powers down the sensing module 900 with the operational circuitry 1214 when the charge level falls below a predetermined threshold. The power management circuitry 1212 subsequently discharges remaining charge on the energy storage device 1210 to prevent unreliable, intermittent, or erratic operation of the operational circuitry 1214.

Under nominal conditions, a charge time from zero charge to fully charged is approximately 3 minutes. In one embodiment, the maximum charge time is specified to be no greater than 7 minutes. The charging time of a capacitively powered system is a major improvement over the two hours or more required to fully charge a battery from zero charge regardless of battery capacity. The capacitive energy storage device 1210 can include capacitors with solid dielectrics to have longer lifetimes than batteries and also when uncharged, regardless of length of time at zero charge. In one arrangement, the wireless charging operation can be performed by electromagnetic induction before removal of any sterile packaging. The capacitive energy storage device 1210 is applicable for powering chronic active implantable devices where data collection is discrete point-of-time measurements rather than continuous, fulltime data collection and storage.

Figure 14:
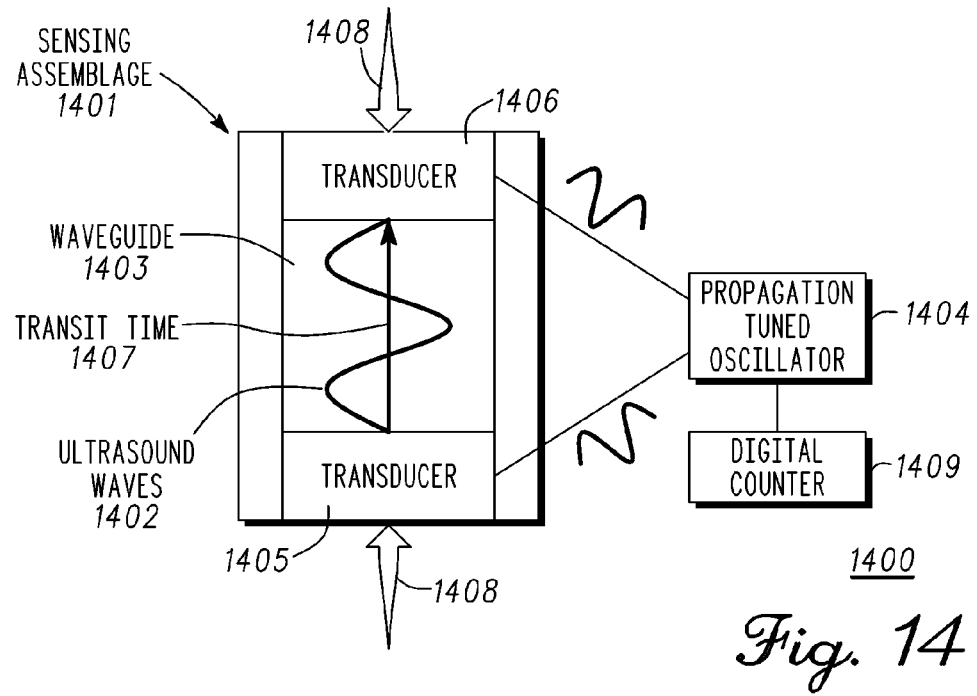
FIG. 14 is an exemplary block diagram of a propagation tuned oscillator (PTO) in accordance with one embodiment.

FIG. 14 is an exemplary block diagram 1400 of a propagation tuned oscillator (PTO) 1404 in accordance with one embodiment. Diagram 1400 illustrates propagation tuned oscillator (PTO) 1404 maintaining positive closed-loop feedback of energy waves 1402 in one or more energy propagating structures 1403 of a sensing assemblage 1401. The sensing assemblage 1401 comprises a first transducer 1405, a second transducer 1406, and a waveguide 1403 (energy propagating structure). First transducer 1405 is coupled to waveguide 1403 at a first location. Second transducer 1406 is coupled to the waveguide 1403 at a second location. The sensing assemblage 1401 is affixed to load bearing or contacting surfaces 1408. External forces applied to the contacting surfaces 1408 compress the waveguide 1403 and change the length of the waveguide 1403. This moves transducers 1405 and 1406 closer to together. The change in length of waveguide 1403 affects the transmit time 1407 of energy waves 1402 propagating between transducers 1405 and 1406. The PTO 1404 in response to these physical changes alters the oscillation frequency of the energy waves 1402 to achieve resonance. In one embodiment, the energy waves 1402 are ultrasonic in frequency. The change in oscillation frequency due to a change in the length of waveguide 1403 is accomplished by way of the PTO 1404 in conjunction with a pulse generator, a mode control, and a phase detector.

Notably, changes in the waveguide 1403 (energy propagating structure or structures) alter the propagation properties of the medium of propagation (e.g. transmit time 1407). Due to the closed-loop operation shown, the PTO 1404 changes the resonant frequency of the oscillator and accordingly the frequency of oscillation of the closed loop circuit. In particular, the PTO 1404 adjusts the oscillation frequency to be an integer number of waves. The digital counter 1409 in conjunction with electronic components counts the number of waves to determine the corresponding change in the length of the waveguide 1403. The change in length of waveguide 1403 is in direct proportion to the external force being applied to surfaces 1408 thus enabling the conversion of changes in parameter or parameters of interest into electrical signals.

Briefly, the operation of propagation tuned oscillator 1404 is disclosed hereinbelow. Transducer 1405 emits energy waves 1402 into waveguide 1403 at the first location. The frequency of ultrasound energy waves 1402 emitted by ultrasound resonator or transducer 1405 is controlled by propagation tuned oscillator 1404. Emitted energy waves propagate from the first location of the waveguide 1403 to the second location. A detecting transducer can be either a separate ultrasound transducer or the emitting transducer 1405 itself depending on the selected mode of propagation. As shown, transducer 1406 is a separate detecting transducer coupled to the second location of waveguide 1403. The transit time 1407 of ultrasound waves 1402 propagating through the waveguide 1403 determines the period of oscillation of propagation tuned oscillator 1404. As previously noted, changes in external forces or conditions applied to surfaces 1408 affect the propagation characteristics of waveguide 1403 and alter transit time 1407. The number of wavelengths of ultrasound energy pulses or waves 1402 is held constant by propagation tuned oscillator 1404. This constraint forces the frequency of oscillation of propagation tuned oscillator 1404 to change when the length of waveguide 1403 is modified. The resulting changes in frequency are captured with digital counter 1409 as a measurement of changes in external forces or conditions applied to surfaces 1408.

FIG. 15 is another exemplary block diagram 1500 of a dual mode closed loop measurement system in accordance with one embodiment. The diagram 1500 illustrates signal paths and interfaces with a propagation tuned oscillator or oscillators that iteratively adjust the repetition rate of energy pulses for measurement of the transit time of energy pulses between two wireless modules. Propagation tuned oscillator 1503 drives the digital interface coupled to the transducer 1504 to provide energy wave or pulse emission into a medium 1505 controlled by wireless module or device 1502. The transducer 1504 contacts or is engaged at an interface 1524 of energy propagating medium 1505.

A measurement process is initiated by the emission of energy pulses or waves 1506 into the medium 1505. In one embodiment, the energy wave propagation occurs of within a body or physical system 1501 such as a muscular-skeletal system or components of artificial orthopedic implants of the muscular-skeletal system. The transit time of energy pulses or waves propagating through the medium 1505 changes as the energy propagation characteristics of medium 1505 are influenced by changes in the parameter or parameters of interest.

The energy waves 1506 are detected by a second energy pulse or wave detecting wireless module or device 1507. Second module 1507 includes a transducer 1508 contacting or engaged with propagating medium 1505 at an interface 1526. Transducer 1508 is coupled to digital circuitry 1509 within wireless module or device 1507 driving a digital interface to a separate transducer 1510. The transducer 1510 is controlled to emit energy of a different form than the energy received from the first wireless module or device 1502. For example, transducer 1508 receives an ultrasonic acoustic energy wave or pulse and transducer 1510 emits an electromagnetic wave. The transducer 1510 emits an energy wave 1511 that corresponds to and is in response to the detection of energy wave or pulse 1506. The energy wave or pulse 1511 is detected by transducer 1512 on wireless module or device 1502. Transducer 1512 is interfaced to propagation tuned oscillator 1503 thus enabling closed-loop control of the stream of energy waves or pulses propagating through medium of propagation 1505. The resulting changes in the repetition rate of operation can be readily captured with digital counter 1509 or accumulator to capture data on the parameter or parameters of interest.

The operation of first module 1502 and second module 1507 for propagating energy waves or pulses through medium 1505 in a positive feedback closed-loop is disclosed further hereinbelow. A clock 1521 provides a pulse A that is coupled to transducer 1504 within the first wireless module or device 1502. The pulse A triggers one or more energy waves or pulses 1506 to be emitted into the medium 1505 at the interface 1524. The energy waves or pulses 1506 propagate in the medium 1505 within the body or physical system 1501 under study. The transit time of energy waves or pulses 1506 depend on the energy propagation characteristics of the propagation medium 1505.

The energy waves or pulses 1506 are detected by the second wireless module or device 1507 when they propagate to the interface 1526. The second wireless module 1507 in response to the received energy wave 1506 emits a different form of energy pulse 1511 back to the first wireless module or device 1502. The energy pulse or wave 1511 is detected by the first wireless module or device 1502 and converted into a digital pulse B. The digital pulse B is compared with the initial pulse A by the phase detector 1514 within the propagation tuned oscillator 1503 within the first wireless module 1502. The phase detector 1514 in view of the phase difference drives changes in the repetition rate of the digital clock 1521 driving the energy transducer 1504 within the first wireless module or device 1502.

The process continues to iterate by way of the PTO 1503 until the phase difference between the energy waves or pulses emitted into the medium 1505 and received by the first wireless module or device 1502 is minimized. The repetition rate of the clock 1521 is measured by accumulating cycle counts by counter 1509 over a known time base. Changes in the parameter or parameters of interest change the propagation characteristics of energy waves or pulses 1506 within the propagation medium 1505 between the two wireless modules or devices 1502 and 1507. The propagation tuned oscillator 1503 continually updates the repetition rate of the digital clock 1521 to reduce phase differences between the energy waves or pulses emitted 1506 and received 1511 by the first wireless module or device 1502. The accumulated count by counter 1509 is transferred to external equipment for additional processing, storage, or display, or combinations of these. The accumulated count within counter 1509 is periodically updated to maintain real-time data on changes in the parameter or parameters of interest.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. An orthopedic screw having threads thereon configured to couple to the muscular-skeletal system comprising:
   a screw including a cavity; and
   a passive circuit within the cavity where the passive circuit is configured to emit an energy wave to the screw and where the screw is configured to couple the energy wave to a medium;
   an inductor; and a transducer operatively coupled to the inductor; and
   further including a flexible substrate where the inductor and transducer are mounted to the substrate and where the substrate includes interconnect for coupling the inductor to the transducer.

2. The orthopedic screw of claim 1 where a die of the inductor and transducer is stacked.

3. The orthopedic screw of claim 1 where a flexible substrate is altered from a planar shape to fit in the cavity of the screw.

4. The orthopedic screw of claim 1 further including a module configured to be in closed-loop feedback with the inductor and the transducer of the orthopedic screw.

5. The orthopedic screw of claim 4 where the module is configured to be coupled in a first path to the inductor of the orthopedic screw electromagnetically.

6. The orthopedic screw of claim 5 where the module is configured to be coupled in a second path to the transducer of the orthopedic screw ultrasonically.

7. The orthopedic screw of claim 6 where the closed-loop feedback between the module and the orthopedic screw forms a propagation tuned oscillator for a continued emission, propagation, and detection of energy waves in the medium and where an energy wave transit time, frequency, or phase is monitored over a predetermined distance through the medium.

8. The orthopedic screw of claim 1 where the orthopedic screw is configured to be used to measure bone density of a muscular-skeletal system.

9. An orthopedic screw comprising:
a screw having a cavity therein; and
a passive circuit comprising an inductor operatively coupled to a transducer within the cavity where the transducer is configured to emit an energy wave to the screw and where the screw is configured to couple the energy wave to a medium;
where the transducer is an ultrasonic transducer; and
further including a flexible substrate where the inductor and transducer are mounted to the substrate and where the substrate includes interconnect for coupling the inductor to the transducer.

10. The orthopedic screw of claim 7 where the transducer is coupled to the screw and where the screw is configured to radiate an ultrasonic signal.

11. The orthopedic screw of claim 10 where the flexible substrate is altered from a planar shape to fit in the cavity of the screw.

12. The orthopedic screw of claim 11 where a die of the inductor and transducer is stacked.

13. The orthopedic screw of claim 9 further including a module configured in closed-loop feedback with the inductor and the transducer of the orthopedic screw.

14. The orthopedic screw of claim 13 where the module is configured to couple in a first path to the inductor of the orthopedic screw electromagnetically and where the module is configured to couple in a second path to the transducer of the orthopedic screw ultrasonically.

15. The orthopedic screw of claim 14 where the module and the screw are configured to form a propagation tuned oscillator for a continued emission, propagation, and detection of energy waves in the medium and where an energy wave transit time, frequency, or phase is monitored over a predetermined distance through the medium.

16. The orthopedic screw of claim 15 where the orthopedic screw is configured to measure bone density of a muscular-skeletal system.

* * * * *